(12) United States Patent
Deng et al.

(10) Patent No.: US 10,871,531 B2
(45) Date of Patent: Dec. 22, 2020

(54) FIXATION MECHANISM AND A MRI SYSTEM

(71) Applicant: KONINKLIJKE PHILIPS N.V., Eindhoven (NL)

(72) Inventors: Wen Deng, Suzhou (CN); Xi Rong Chen, Kunshan (CN)

(73) Assignee: Koninklijke Philips N.V., Eindhoven (NL)

( * ) Notice: Subject to any disclaimer, the term of this patent is extended or adjusted under 35 U.S.C. 154(b) by 459 days.

(21) Appl. No.: 15/412,096

(22) Filed: Jan. 23, 2017

(65) Prior Publication Data

US 2018/0210043 A1 Jul. 26, 2018

(51) Int. Cl.
  *G01R 33/34* (2006.01)
  *G01R 33/28* (2006.01)
  *A61B 5/055* (2006.01)

(52) U.S. Cl.
  CPC ........ *G01R 33/34084* (2013.01); *A61B 5/055* (2013.01); *A61B 5/0555* (2013.01); *G01R 33/28* (2013.01); *G01R 33/34007* (2013.01)

(58) Field of Classification Search
  CPC ..... A61B 5/055; A61B 5/0555; A61B 6/0421; A61B 6/04
  USPC ................................. 600/415, 422
  See application file for complete search history.

(56) References Cited

U.S. PATENT DOCUMENTS

| | | | |
|---|---|---|---|
| 5,137,442 A | 8/1992 | Starkey | |
| 7,174,587 B2 * | 2/2007 | Tybinkowski | A61B 6/0421 5/601 |
| 7,697,971 B1 * | 4/2010 | Green, Jr. | A61B 5/0555 324/307 |
| 8,290,569 B2 * | 10/2012 | Piron | G01R 33/36 600/415 |
| 9,943,369 B2 * | 4/2018 | Heigl | A61B 5/055 |
| 2003/0204136 A1 * | 10/2003 | Green | A61B 5/0555 600/415 |
| 2004/0143905 A1 | 7/2004 | Pastyr et al. | |
| 2008/0191696 A1 * | 8/2008 | Van Der Burgt | B60N 3/008 324/318 |
| 2008/0214925 A1 * | 9/2008 | Wilson | A61B 90/36 600/410 |

(Continued)

FOREIGN PATENT DOCUMENTS

WO 2009128166 A1 10/2009

*Primary Examiner* — John R Downey (57) ABSTRACT

A fixation mechanism (5) fixes a flex coil unit of a MRI system onto a patient. An oblique-shaped clip (9) includes a first portion (9a) and a second portion (9b) arranged to form an oblique angle therebetween. The first portion (9a) is configured to be arranged with a strap (7) along which the oblique-shaped clip (9) is subject to a force when the flex coil unit is fixed onto the patient. An elongated slot (11) is located at a longitudinal side of a housing of a spine coil unit of the MRI system and formed at least partially by the housing of the spine coil unit. The elongated slot (11) is configured to receive the second portion (9b) of the oblique-shaped clip (9) and further configured to allow the second portion (9b) of the oblique-shaped clip (9) to abut against a side wall of the elongated slot (11) by the force along the strap (7). An operator conveniently inserts the clip into the slot or release the clip out of the slot at any position along the longitudinal direction of the housing.

19 Claims, 7 Drawing Sheets

(56) References Cited

U.S. PATENT DOCUMENTS

| | | | |
|---|---|---|---|
| 2012/0265052 A1* | 10/2012 | Rohr | A61B 5/0555 |
| | | | 600/415 |
| 2012/0315080 A1* | 12/2012 | Zink | A61B 5/055 |
| | | | 403/110 |
| 2014/0361769 A1* | 12/2014 | Hardie | G01R 33/3692 |
| | | | 324/307 |
| 2015/0164725 A1* | 6/2015 | Wilson | A61G 13/129 |
| | | | 128/845 |
| 2016/0022170 A1* | 1/2016 | Candidus | A61B 5/0555 |
| | | | 600/415 |
| 2016/0054404 A1* | 2/2016 | Duensing | G01R 33/34046 |
| | | | 324/309 |
| 2018/0035911 A1* | 2/2018 | Nousiainen | A61B 5/0555 |

* cited by examiner

FIXATION MECHANISM AND A MRI SYSTEM

CROSS-REFERENCE TO PRIOR APPLICATIONS

This application claims the benefit or priority of PCT/CN2016/072550 filed Jan. 28, 2016 and EP patent application Ser. No. 16163190.8 filed Mar. 31, 2016 all of which are incorporated herein in whole by reference.

FIELD OF THE INVENTION

The invention relates to a magnetic resonance imaging (MRI) system, in particular to a fixation mechanism for fixing a flex coil unit of a MRI system onto a patient.

BACKGROUND OF THE INVENTION

Magnetic resonance imaging is a non-invasive imaging technique that may be used to display detailed tissue structures in the body of a patient. The displayed tissue structure may provide valuable information assisting in the diagnosis and treatment of various medical conditions.

Before a MRI system scans a patient, a flex coil unit such as a torso coil unit, a muscle skeleton coil unit or a sensor flex coil unit is usually placed on a body of the patient lying on a tabletop of the MRI system and is held in place by means of a fixation mechanism to finish the scanning. A conventional fixation mechanism generally comprises two straps, an inverted T-shaped clip attached to an end of each one of the two strap and two dovetailed grooves formed in the tabletop. A size-increased portion is formed at one end of the two dovetailed grooves to insert the inverted T-shaped clip into the respective dovetailed groove or release the inverted T-shaped clip from the respective dovetailed groove.

Before scanning, the inverted T-shaped clip has to be inserted into the respective dovetailed groove from the size-increased portion formed at one end of the dovetailed groove and be moved along the dovetailed groove toward a position at which the flex coil unit is placed. At this position, the two straps are pulled and connected together at their free end by a known way to hold the flex coil unit in place on the body of the patient. After scanning, the two straps are loosed, the inverted T-shaped clip is moved along the dovetailed groove toward the size-increased portion to release the inverted T-shaped clip from the dovetailed groove and remove the flex coil unit from the body of the patient. The insertion and release of the inverted T-shaped clip is very troublesome and inconvenient for an operator. Furthermore, as a result of the dovetailed grooves generally machined in the tabletop, it is very hard to form the dovetailed grooves and control the quality thereof. And, if the dovetailed grooves forming a part of the tabletop are damaged, the tabletop has to be replaced as a whole.

Thus, there is a need to make improvements on the conventional fixation mechanism for fixing the flex coil unit of the MRI system onto the patient.

SUMMARY OF THE INVENTION

According to one aspect of the present invention, it is to provide a fixation mechanism for fixing a flex coil unit of a MRI system onto a patient comprising:

an oblique-shaped clip comprising a first portion and a second portion arranged to form an oblique angle therebetween, wherein the first portion is configured to be arranged with a strap along which the clip is subject to a force when the flex coil unit is fixed onto the patient; and an elongated slot located at a longitudinal side of a housing of a spine coil unit of the MRI system and formed at least partially by the housing of the spine coil unit, the elongated slot being configured to receive the second portion of the oblique-shaped clip and further configured to allow the second portion of the oblique-shaped clip to abut against a side wall of the elongated slot by the force along the strap.

According to other aspect of the present invention, it is to provide a fixation mechanism for fixing a flex coil unit of a MRI system onto a patient comprising:

an oblique-shaped clip comprising a first portion and a second portion arranged to form an oblique angle therebetween, wherein the first portion is configured to be arranged with a strap along which the oblique-shaped clip is subject to a force when the flex coil unit is fixed onto the patient; and an elongated slot located at a longitudinal side of a housing of a tabletop of the MRI system and formed at least partially by the housing of the tabletop, the elongated slot being configured to receive the second portion of the oblique-shaped clip and further configured to allow the second portion of the oblique-shaped clip to abut against a side wall of the elongated slot by the force along the strap.

According to the present invention, the clip may be inserted into or released out of the elongated slot at any position along the longitudinal direction of the housing of the spine coil unit or the tabletop, e.g., directly inserted into or released out of the elongated slot at an operative position where the clip is positioned for fixing the flex coil to a predetermined position on the patient. Thus, the insertion and release of the clip is very convenient and easy for the operator.

Preferably, the elongated slot is shaped to match with the second portion of the clip, which facilitates the second portion of the clip to smoothly insert into or release out of the elongated slot.

Preferably, the second portion of the clip is arc-shaped, which may prevent more reliably the second portion of the clip from being released out of the elongated slot. Preferably, the second portion of the clip comprises a first toothed surface, the side wall of the elongated slot facing the first toothed surface comprises a second toothed surface, the first toothed surface engages with the second toothed surface when the second portion of the clip abuts against the side wall of the elongated slot. Engagement between the first toothed surface and second toothed surface further prevent the clip from being pulled inadvertently out of the slot.

Preferably, a surface of the second portion of the clip and a surface of the slot facing each other are roughened to increase a friction force between them when the second portion of the clip abuts against the side wall of the elongated slot.

Preferably, the clip further comprises a supported portion projecting from a joint of the first portion and the second portion, the supported portion is supported by the housing when the clip is inserted into the elongated slot. The supported portion may prevent the second portion from being damaged by decreasing a force acting on the second portion.

Preferably, the clip further comprises a projection extending from a bottom of the first portion, the housing comprises an elongated receiving groove for receiving the projection when the clip is inserted into the elongated slot. It is possible to further prevent the clip coming out of the slot by receiving the projection into the elongated receiving groove.

Preferably, the elongated slot is defined by the housing and an elongated body. In this way, the elongated slot is defined by two separate members. Preferably, the housing comprises a supporting portion laterally projecting from each side of a main body of the housing along its longitudinal direction, the elongated body is fixed removably onto the supporting portion so that the elongated slot is defined between the main body of the housing and the elongated body. It is unnecessary to replace both of the two members when one of them is damaged.

Preferably, the supporting portion together with the main body of the housing defines an elongated cavity to receive the elongated body. In this way, the elongated body is invisible from the housing.

Preferably, an engaging mechanism is formed between the elongated body and the supporting portion, which help quick positioning and assembly of the elongated body.

Preferably, the clip further comprises a projection extending from a bottom of the first portion, the elongated body comprises an elongated receiving groove for receiving the projection when the clip is inserted into the elongated slot. It is possible to further prevent the clip coming out of the slot by receiving the projection into the elongated receiving groove.

Preferably, the fixation mechanism further comprises a strap attached to the first portion of the clip.

According to other aspect of the present invention, it is to provide a MRI system comprising the above-mentioned fixation mechanism for fixing the flex coil unit of the MRI system onto the patient.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

A magnetic resonance imaging (MRI) system generally comprises a housing defining an examination space for receiving a patient to be examined, a magnetic field generating system for generating a magnetic field in the examination space, and an electromagnetic resonance receiving system which comprises at least one dedicated receiving coil unit. Before scanning, the patient lies on a tabletop of the MRI system, a coil unit is placed on the body of the patient and is held in place by a fixation mechanism. Then the patient lying on the tabletop is delivered into the examination space to be scanned and imaged. After scanning, the patient lying on the tabletop is delivered out of the examination space and the coil unit is released from the body of the patient. The invention involves mainly the fixing of the coil unit on the body of the patient, in particular a fixation mechanism for fixing a flex coil unit of the MRI system onto the patient. Other parts of the MRI system are well known and the description thereof therefore is omitted.

Figure 1:
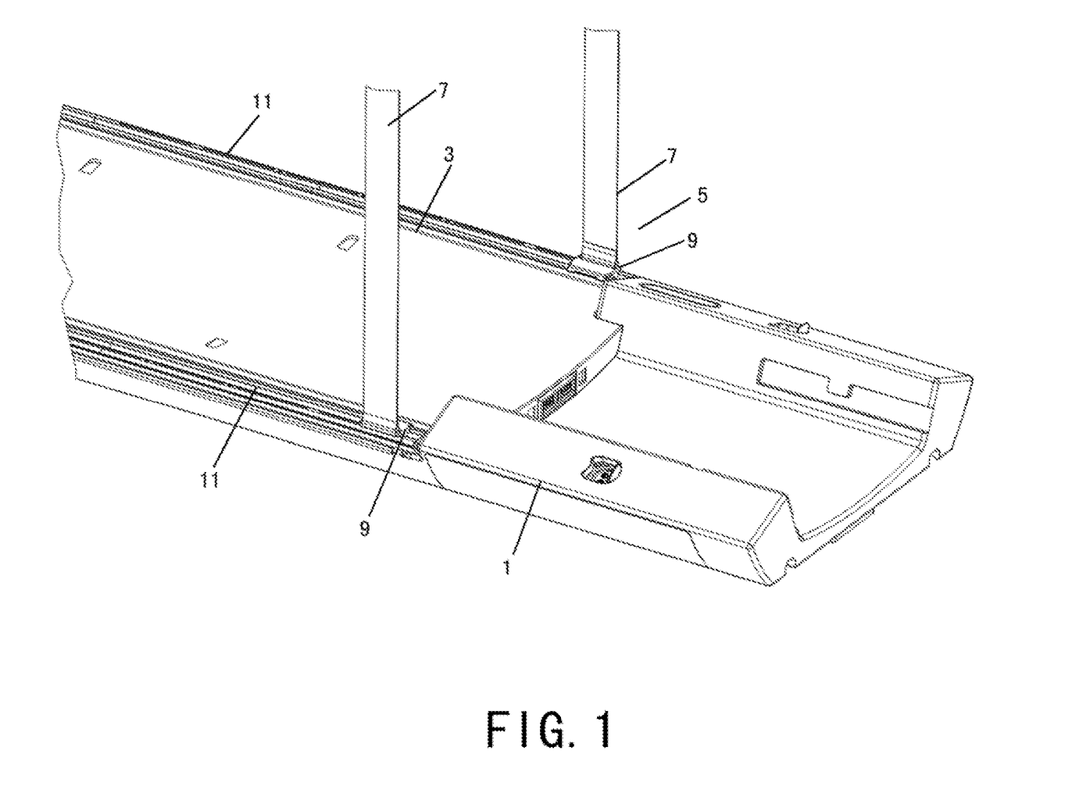
FIG. 1 is a perspective view showing schematically a tabletop of a MRI system and a spine coil unit placed on the tabletop, wherein the spine coil unit is provided with a fixation mechanism for fixing a flex coil unit of the MRI system onto a patient according to the present invention.
Figure 2:
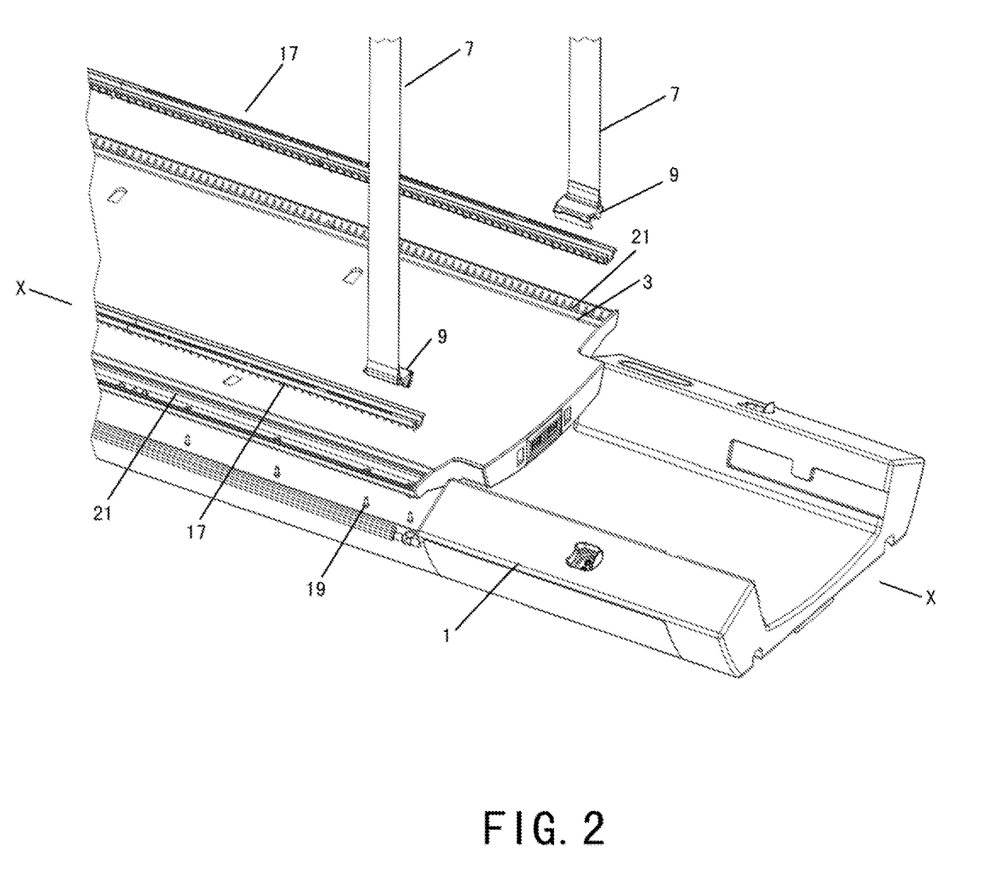
FIG. 2 is an exploded perspective view of the tabletop and the spine coil unit shown in FIG. 1.
Figure 3:
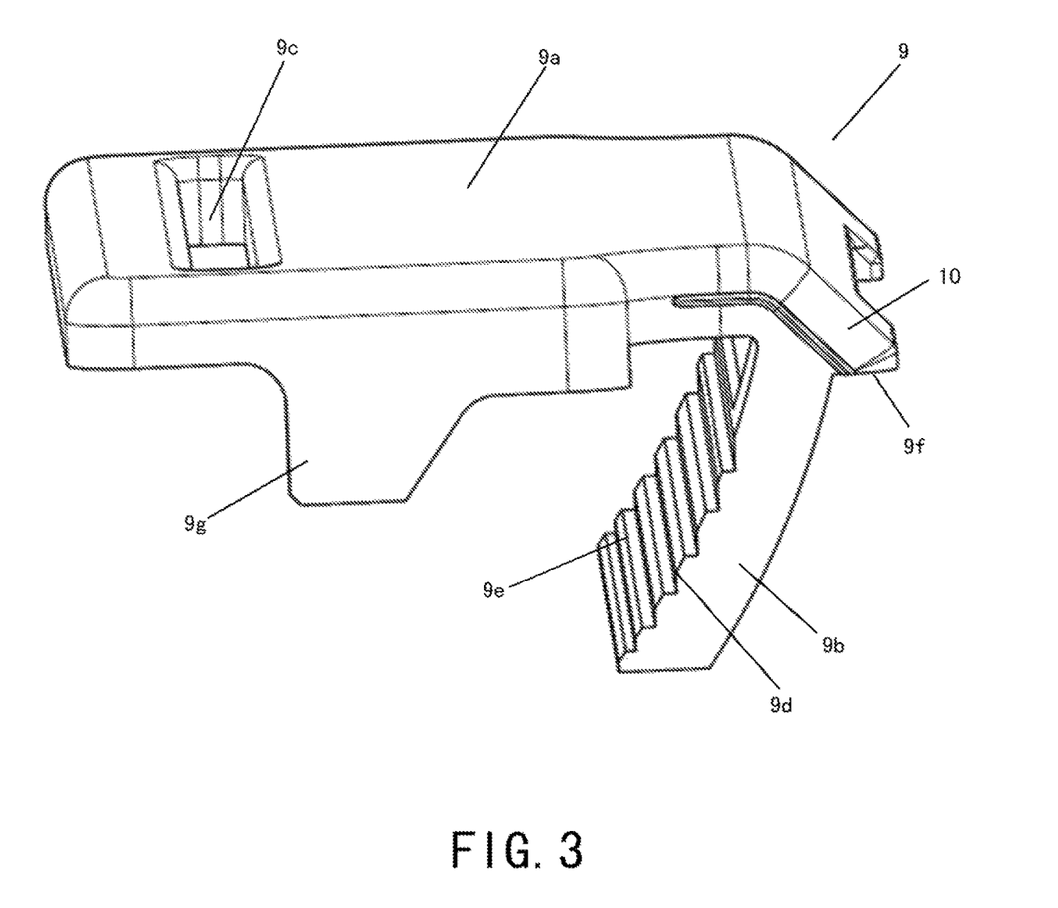
FIG. 3 is a perspective view showing schematically a clip of the fixation mechanism according to the present invention.

FIG. 1 is a perspective view showing schematically a tabletop of a MRI system and a spine coil unit placed on the tabletop, wherein the spine coil unit is provided with a fixation mechanism for fixing a flex coil unit of the MRI system onto a patient according to the present invention. FIG. 2 is an exploded perspective view of the tabletop and the spine coil unit shown in FIG. 1. As shown in FIGS. 1 and 2, although a tabletop 1 of the MRI system may support directly the patient, a spine coil unit 3 is always placed onto the tabletop 1 because the spine coil unit 3 is too heavy to handle easily. Thus the patient usually lies on the spine coil unit 3 placed onto the tabletop 1 when being scanned. A flex coil unit (not shown) such as a torso coil unit, a muscle skeleton coil unit or a sensor flex coil unit is placed on the body of the patient lying on the spine coil unit 3 and held in place by a fixation mechanism 5 for fixing the flex coil unit onto the patient according to the present invention. The fixation mechanism 5 for fixing the flex coil unit onto the patient according to the present invention comprise two straps 7 and a clip 9 attached to an end of each one of the two straps 7. FIG. 3 is a perspective view showing schematically the clip 9 of the fixation mechanism according to the present invention. As shown in FIG. 3, the clip 9 comprises a first portion 9a and a second portion 9b. The second portion 9b extends from the first portion 9a and is inclined relative to the first portion 9a. Preferably, the clip 9 is substantially 7-shaped. More preferably, the angle between the first portion 9a and the second portion 9b is not equal to 90°. In other words, the clip 9 is oblique-shaped. One end of the strap 7 is attached to the first portion 9a. A hole 9c may be formed at the first portion 9a to receive the strap 7. Of course, the strap 7 may be fixed directly at the first portion 9a. The fixation mechanism 5 for fixing the flex coil unit onto the patient according to the present invention further comprise two elongated slots 11 defined respectively in two longitudinal sides of the spine coil unit 3 to receive the second portion 9b of the respective clip 9.

Figure 4:
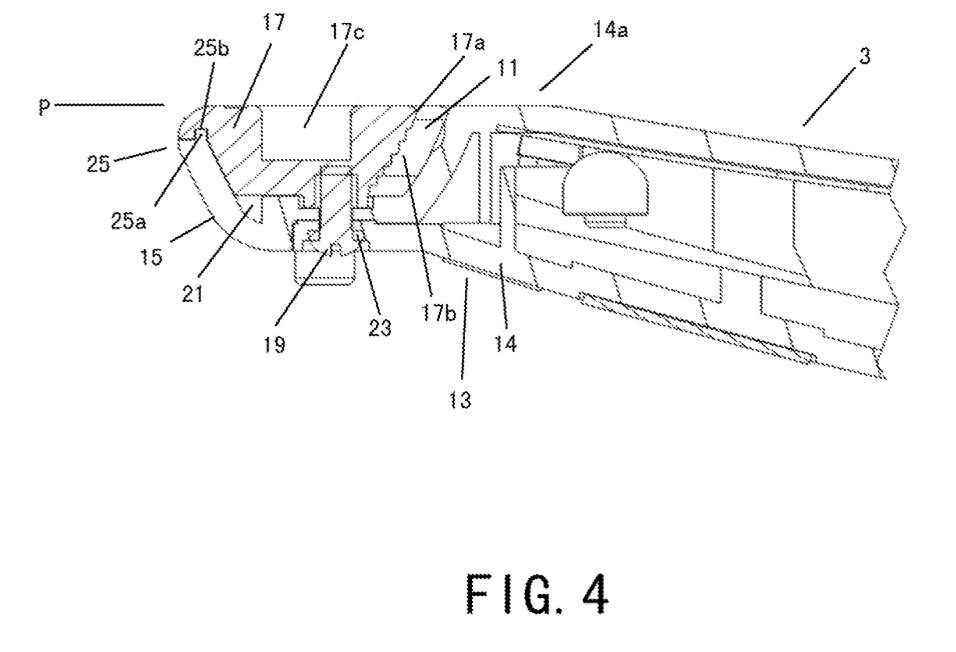
FIG. 4 is a partial cross-sectional view of the spine coil unit showing schematically a slot for receiving a clip of the fixation mechanism.
Figure 5:
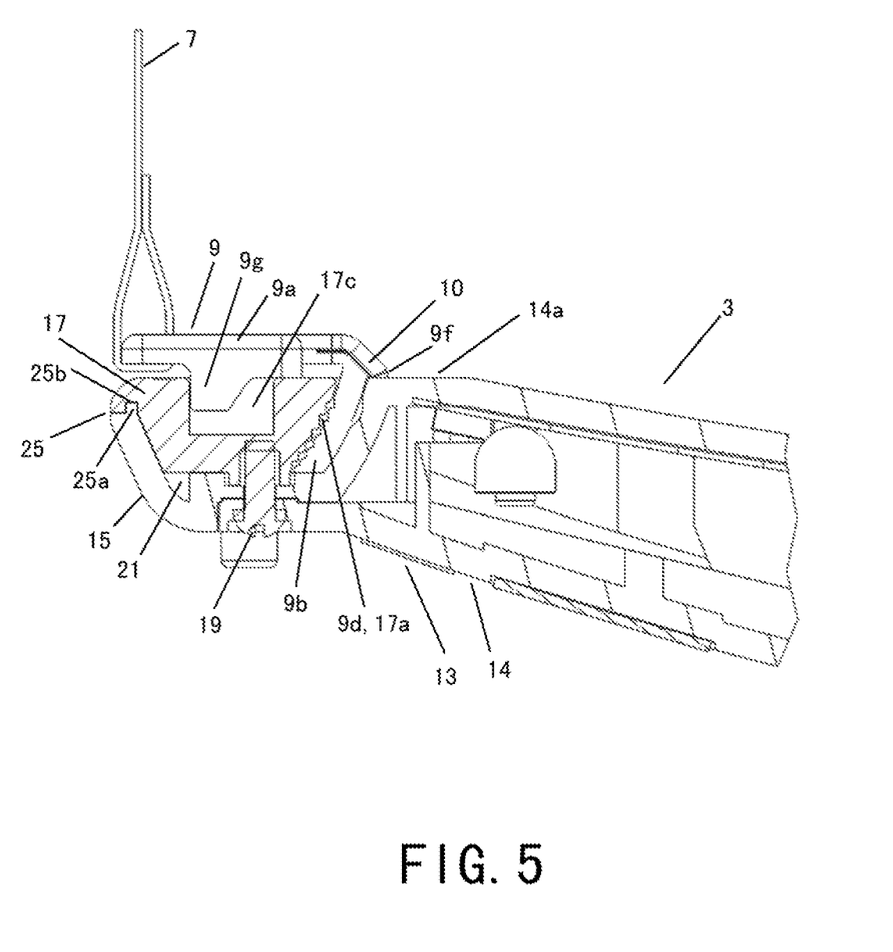
FIG. 5 is a cross-sectional view similar to FIG. 4 with the clip of the fixation mechanism being inserted into the slot.
Figure 6:
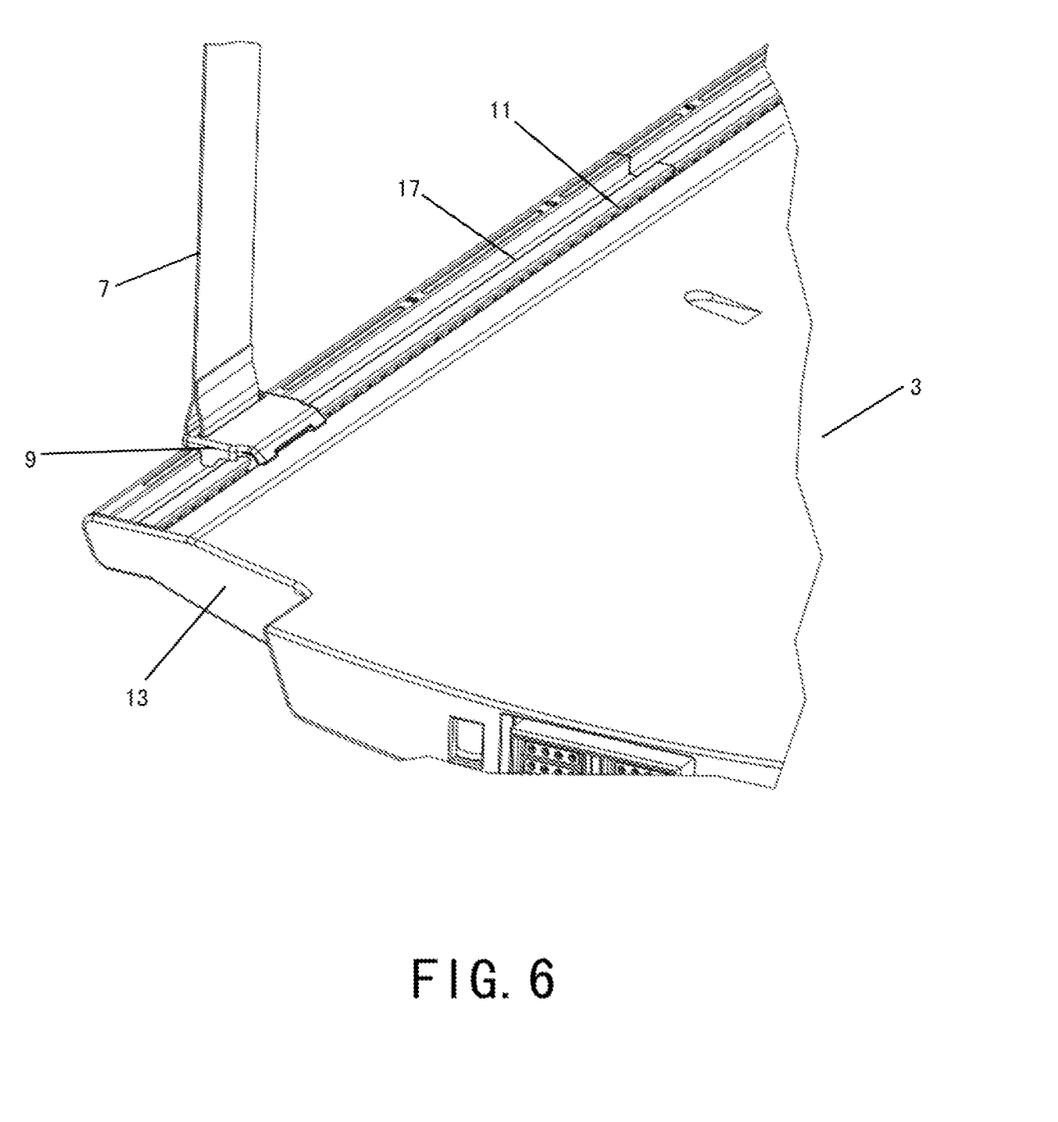
FIG. 6 is a partial perspective view of the spine coil unit showing schematically the clip of the fixation mechanism being inserted into the slot.

FIG. 4 is a partial cross-sectional view of the spine coil unit showing schematically a slot for receiving the clip 9 of the fixation mechanism 5. The spine coil unit 3 comprises a housing 13 and a spine coil (not shown) housed in the housing 13. The housing 13 further comprises a main body 14 and a supporting portion 15 laterally projecting from each side of the main body 14 along a longitudinal direction of the main body 14. The longitudinal direction of the main body 14 of the housing 13 is the same as a longitudinal direction XX of the tabletop 1 as shown in FIG. 2. An elongated body 17 may be fixed removably onto the supporting portion 15 by screws 19 so that the elongated slot 11 is defined between the main body 14 of the housing 13 and the elongated body 17. When the flex coil is placed and fixed onto the patient, the clip 9 is at an operative position where the second portion 9b of the clip 9 is inserted and held in the elongated slot 11 while the first portion 9a of the clip 9 is subject an upward force. The elongated slot 11 is preferably inclined relative to a plane P on which a top 14a of the main body 14 of the housing 13 is located, as shown in FIG. 4. In one embodiment, the elongated slot 11 is arranged to form the oblique angle coperatievey with a tope surface of the table top or the spine coil, which mates with the oblique-shaped clip 9 when the clip 9 is inserted into the elongnated slot 11. The width of the elongated slot 11 is slightly larger than the thickness of the second portion 9b of the respective clip 9 so that the second portion 9b of the respective clip 9 is inserted freely into or released freely out of the elongated slot 11 when the respective strap 7 is in an inoperative state. In the inoperative state, the respective strap 7 is subject to no force and is loosed. FIG. 5 is a cross-sectional view similar to FIG. 4 with the clip of the fixation mechanism being inserted into the slot and in an operative state. FIG. 6 is a partial perspective view of the spine coil unit showing schematically the clip of the fixation mechanism being inserted into the slot. As shown in FIGS. 5 and 6, the second portion 9b of the respective clip 9 is inserted into the elongated slot 11 defined between the main body 14 of the housing 13 and the elongated body 17 while the flex coil unit is placed onto the patient. In the operative state, the two straps 7 are pulled and connected together to hold the flex coil unit in place on the patient. At the same time, a force such as a upward pull force is applied to the respective strap and therefore to the first portion 9a of the clip 9 so that the clip 9 is moved until the second portion 9b of the clip 9 abuts against a side wall of the elongated slot 11, thereby preventing the second portion 9b of the clip 9 from being released out of the elongated slot 11.

The second portion 9b of the clip 9 and the elongated slot 11 may have a similar shape, i.e., the elongated slot 11 may be shaped to match with the second portion 9b of the clip 9. As shown in FIG. 3, the second portion 9b of the clip 9 is substantially arc-shaped. Similarly, the elongated slot 11 is also substantially arc-shaped to match with the substantially arc-shaped second portion 9b of the clip 9. When the strap 7 is in the operative state, engagement between the substantially arc-shaped second portion 9b and the substantially arc-shaped elongated slot 11 prevents more reliably the second portion 9b of the clip 9 from being released out of the elongated slot 11. Of course, it is feasible that both the second portion 9b of the clip 9 and the elongated slot 11 are rectilinear.

A surface 9d of the second portion 9b of the clip 9 facing the elongated body 17 may be provided with one or more teeth 9e. Similarly, a surface 17a of the elongated body 17 defining the elongated slot 11 may also be provided with one or more teeth 17b. The surface 17a of the elongated body 17 forms a side wall defining the elongated slot 11. When the second portion 9b of the respective clip 9 is inserted into the elongated slot 11 and the strap 7 is in the operative state, the toothed surface 9d of the second portion 9b engages with the toothed surface 17a of the elongated body 17 to prevent the second portion 9b of the clip 9 from being pulled inadvertently out of the slot 11. Further, the surface 17a of the elongated body 17 and the surface 9d of the second portion 9b of the clip 9 may be roughened to increase a friction force between them.

The supporting portion 15 together with the main body 14 of the housing 13 may define an elongated cavity 21 to receive the elongated body 17. The screws 19 may be threaded into the elongated body 17 through a hole 23 in the supporting portion 15 to fix the elongated body 17 onto the supporting portion 15. To quickly and properly position the elongated body 17 on the supporting portion 15, an engaging mechanism 25 may be formed between the elongated body 17 and the supporting portion 15. In the preferred embodiment shown in the drawings, the engaging mechanism 25 comprises a positioning projection 25a formed on the supporting portion 15 and a positioning groove 25b formed on the elongated body 17 to receive the positioning projection 25a. Of course, it is feasible that the positioning projection 25a is formed on the elongated body 17 and the positioning groove 25b is formed on the supporting portion 15.

Figure 7:
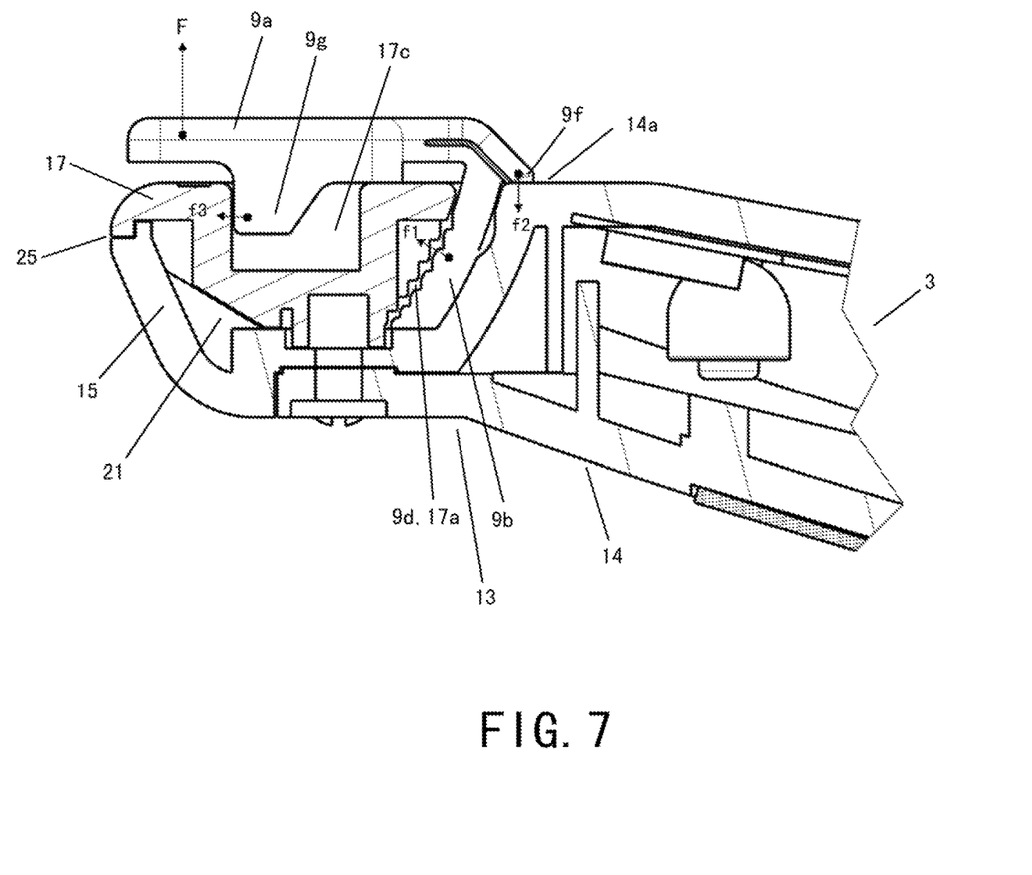
FIG. 7 is a cross-sectional view similar to FIG. 5 showing schematically a distribution of forces acting on the fixation mechanism.

FIG. 7 is a cross-sectional view similar to FIG. 5 showing schematically a distribution of forces acting on the fixation mechanism. As shown in FIG. 7, when the two straps 7 are pulled and connected together, the free end of the first portion 9a of the clip 9 is subject to the upward force F, and at least an aslant upward force f1 is reacted to the elongated body 17. As a result, there is no pull force acting on the clip 9 along an inclined direction of the slot 11 so that the clip 9 does not come out of the slot 11. Preferably, the clip 9 further comprises a supported portion 9f projecting from a joint 10 of the first portion 9a and the second portion 9b. When the second portion 9b of the respective clip 9 is inserted into the elongated slot 11 and the two straps 7 are pulled and connected together, the clip 9 may pivot on the supported portion 9f supported by the main body 14 of the housing 13 until the second portion 9b of the respective clip 9 abut against the side wall of the elongated slot 11. When the supported portion 9f is supported by the main body 14 of the housing 13 of the spine coil unit 3, a downward force f2 is reacted to the housing 13. In this way, the aslant upward force f1 may be decreased to prevent the second portion 9b from being damaged. Further, the clip 9 further comprises a projection 9g extending from a bottom of the first portion 9a, the elongated body 17 comprises an elongated receiving groove 17c for receiving the projection 9g extending from the bottom of the first portion 9a. When the second portion 9b of the clip 9 is inserted into the elongated slot 11 and the free end of the first portion 9a of the clip 9 is subject to the upward force F, a further substantially horizontal force f3 is reacted to the elongated body 17, thereby further preventing the clip 9 coming out of the slot 11. When the two straps 7 are in the inoperative state and thus are loosed, the upward force F is released and the forces f1, f2 and f3 disappear. The clip 9 may be removed freely out of the slot 11 by pulling the clip 9 upward along the inclined direction of the slot 11.

According to the present invention, the clip may be inserted into or released out of the elongated slot at any position along the longitudinal direction of the spine coil unit. Thus, the insertion and release of the clip is very convenient and easy for the operator.

Further, in the above-mentioned preferred embodiments, the elongated body 17 is a separate member that is made by injection moulding and assembled to the spine coil unit. The elongated body is easy for manufacturing and quality control. And, even if the elongated body is damaged, it is not necessary to replace the whole spine coil unit. Advantageously, the maintenance only involves replacing the elongated body, which is cost-effective and convenient. Of course, it should be understood that the elongated body may form a portion of the housing of the spine coil unit and thus is formed integrally with the housing of the spine coil unit.

In the above-mentioned preferred embodiments, the slot for receiving the clip is formed in housing of the spine coil unit. It should be understood that the slot for receiving the clip may be formed in the housing of the tabletop, for example, defined between the housing of the tabletop and the elongated body supported on the housing of the tabletop.

In the above-mentioned preferred embodiments, the fixation mechanism comprises two straps each with one clip attached to one end thereof. It should be understood that the fixation mechanism may comprise only one strap. In such case, the end of the strap having no clip may be pulled and tied to the housing of the spine coil unit or the tabletop. Further, the fixation mechanism according to the present invention is not limited to fix the flex coil unit of the MRI system onto the patient, it may be used to fix any object which is removed subsequently. In such a case, the slot for receiving the clip may be formed at least partially by any suitable receiving member. In the present invention, the receiving member means a member which is used to define separately the elongated slot or define the elongated slot together with the elongated body.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

The invention claimed is:

1. A fixation mechanism for fixing a flex coil unit of a MRI system onto a patient comprising:
an oblique-shaped clip comprising a first portion and a second portion rigidly connected at a junction, the first and second portions extending an oblique angle to each other, a projection rigidly connected adjacent the junction and extending opposite to the first portion, wherein the first portion is configured to be connected with a strap when the flex coil unit is fixed onto the patient; and
an elongated slot defined in a longitudinal surface defined at least partially by a housing of the MRI system, an axis of the elongated slot extending at the oblique angle to the longitudinal surface and being wider than a thickness of the second portion such that the elongated slot is configured to receive the second portion of the oblique-shaped clip with the first portion and the projection of the oblique-shaped clip extending along the longitudinal surface on opposite sides of the junction such that a force on the strap away from the longitudinal surface urges the projection to engage the longitudinal surface and the clip to pivot about the projection on the longitudinal surface urging the second portion of the oblique-shaped clip to abut against a first side wall of the elongated slot closest to the first portion with increased frictional engagement and to decrease frictional engagement with a second side wall opposite to the first side wall.

2. A fixation mechanism for fixing a flex coil unit of a MRI system onto a patient comprising:
an elongated slot extending from a longitudinal surface formed at least partially by a housing of the MRI system, an axis of the elongated slot extending at an oblique angle relative to the longitudinal surface;
an oblique-shaped clip comprising a first portion and a second portion forming the oblique angle therebetween, the first portion being configured to be connected with a strap, the second portion being configured to be slidingly received when the strap is not under tension in the slot with the first portion extending along and overlaying the longitudinal surface to a first side of the slot, the oblique-shaped clip further including a projection extending along and overlaying the longitudinal surface on a second side of the slot across the slot from the first side of the slot, the oblique-shaped clip being configured to pivot about the projection as the projection engages the longitudinal surface causing the second portion to abut and frictionally engage against a side wall of the elongated slot with sufficient frictional engagement with the side wall to forestall removal of the second portion from the elongated slot when the strap is under tension.

3. The fixation mechanism according to claim 1, wherein the elongated slot is defined between the housing and an elongated body removably connected to the housing such that the force along the strap urges the second portion to frictionally engage a wall portion of the slot defined by the elongated body.

4. The fixation mechanism according to claim 1, wherein the second portion of the clip and the elongated slot are arc-shaped.

5. The fixation mechanism according to claim 1, wherein the second portion of the clip comprises a first toothed surface, the side wall of the elongated slot facing the first toothed surface comprises a second toothed surface, the first toothed surface engages with the second toothed surface when the second portion of the clip abuts against the side wall of the elongated slot.

6. The fixation mechanism according to claim 1, wherein a surface of the second portion of the clip and a surface of the slot facing each other are roughened surfaces to increase a friction force between them when the second portion of the clip abuts against the side wall of the elongated slot.

7. The fixation mechanism according to claim 1, wherein the housing is a housing of one of a spine coil unit and a subject supporting table top.

8. The fixation mechanism according to claim 1, wherein the clip further comprises a second projection extending from a bottom of the first portion, the housing comprises an elongated receiving groove for receiving the second projection when the oblique-shaped clip second portion is received in the elongated slot.

9. A fixation mechanism for fixing a coil unit of an MRI system to a patient, the MRI housing including a supporting portion laterally projecting from a longitudinal side of a main body of the housing along a longitudinal direction, the fixing mechanism comprising:
an elongated body fixed removably onto the supporting portion so that an elongated slot is defined between the main body of the housing and the elongated body, the elongated slot extending at an oblique angle to a longitudinal plane defined by the elongated body and the supporting portion;
an oblique-shaped clip in a first portion and a second portion extending at an oblique angle to each other, the second portion being configured to be slidingly received in the slot, the first portion being configured to overlay the elongated body when the second portion is received in the slot, the oblique-shaped clip further including a projection configured to overlay the main body of the housing when the second portion is received in the slot such that a force transverse to the longitudinal plane on the first portion causes the clip to pivot such that the projection is pressed against the main body and the second portion frictionally engages a side of the slot defined by the elongated body.

10. The fixation mechanism according to claim 9, wherein the supporting portion together with the main body of the housing defines an elongated cavity to receive the elongated body.

11. The fixation mechanism according to claim 9, wherein an engaging mechanism is formed between the elongated body and the supporting portion.

12. The fixation mechanism according to claim 3, wherein the clip further comprises a second projection extending from a bottom of the first portion, the elongated body comprises an elongated receiving groove for receiving the second projection when the clip second portion is inserted into the elongated slot.

13. A MRI system comprising a fixation mechanism according to claim 1.

14. The fixation mechanism according to claim 2, wherein the second portion of the clip and the elongated slot are arc-shaped.

15. The fixation mechanism according to claim 2, wherein the second portion of the clip comprises a first toothed surface, the side wall of the elongated slot facing the first toothed surface comprises a second toothed surface, the first toothed surface engages with the second toothed surface when the second portion of the clip abuts against the side wall of the elongated slot.

16. The fixation mechanism according to claim 2, wherein a surface of the second portion of the clip and a surface of the slot facing each other are roughened surfaces to increase a friction force engagement between them when the second portion of the clip abuts against the side wall of the elongated slot when the strap is under tension.

17. The fixation mechanism according to claim 2, wherein the tension along the strap urges the oblique-shaped clip to urge the second portion into greater frictional engagement with the side wall of the elongated slot in response to greater tension on the strap.

18. The fixation mechanism according to claim 2, wherein the housing is a housing of one of a spine coil unit and a subject supporting table top.

19. A MRI system comprising a fixation mechanism according to claim 2.

* * * * *